United States Patent
Gu et al.

(10) Patent No.: US 12,285,450 B2
(45) Date of Patent: Apr. 29, 2025

(54) LACTIPLANTIBACILLUS PLANTARUM EFFECTIVELY INHIBITING MULTI-DRUG-RESISTANT KLEBSIELLA PNEUMONIAE AND USE THEREOF

(71) Applicant: Zhejiang Gongshang University, Zhejiang (CN)

(72) Inventors: Qing Gu, Zhejiang (CN); Yingjuan Zhang, Zhejiang (CN); Qingqing Zhou, Zhejiang (CN); Zhongdu Ye, Zhejiang (CN); Ping Li, Zhejiang (CN)

(73) Assignee: Zhejiang Gongshang University, Hangzhou (CN)

( * ) Notice: Subject to any disclaimer, the term of this patent is extended or adjusted under 35 U.S.C. 154(b) by 0 days.

(21) Appl. No.: 18/895,456

(22) Filed: Sep. 25, 2024

(65) Prior Publication Data

US 2025/0099519 A1    Mar. 27, 2025

(30) Foreign Application Priority Data

Sep. 25, 2023 (CN) .................. 202311234569.X

(51) Int. Cl.
*A61K 35/747* (2015.01)
*A61P 31/04* (2006.01)

(52) U.S. Cl.
CPC ............ *A61K 35/747* (2013.01); *A61P 31/04* (2018.01)

(58) Field of Classification Search
None
See application file for complete search history.

(56) References Cited

FOREIGN PATENT DOCUMENTS

| | | |
|---|---|---|
| CN | 102690771 A | 9/2012 |
| CN | 107312726 A | 11/2017 |
| CN | 111394361 A | 7/2020 |
| CN | 112852685 A | 5/2021 |
| CN | 115851494 A | 3/2023 |
| CN | 116004430 A | 4/2023 |
| CN | 116083273 A | 5/2023 |
| CN | 116396894 A | 7/2023 |
| CN | 116790425 A | 9/2023 |
| KR | 20210138857 A | 11/2021 |

OTHER PUBLICATIONS

Mona Mohiedden Abdelhalim et al., In vitro antibacterial effect of probiotics against Carbapenamase-producing multidrug-resistant Klebsiella pneumoniae clinical isolates, Cairo, Egypt, Journal of the Egyptian Public Health Association, 2022, pp. 1-7, vol. 97, No. 19.
Yu Zhang, The study of antibacterial metabolite of Lactobacillus plantarum and it's clinical application, Dissertation for the Degree of Master of Shanghai Jiao Tong University, China Academic Journal Electronic Publishing House, Apr. 2016.

*Primary Examiner* — Oluwatosin A Ogunbiyi

(57) ABSTRACT

A *Lactiplantibacillus plantarum* strain ZFM518 deposited under CCTCC NO: M 2022442 is provided. Also provided is a composition including the strain ZFM518. Further provided is a method of treating a subject infected by *Klebsiella pneumoniae* ZFM4 deposited under CCTCC NO: M 20221900, including administrating to the subject a composition comprising a therapeutically effective amount of a fermentation supernatant of the *Lactiplantibacillus plantarum* strain ZFM518.

3 Claims, 6 Drawing Sheets

A

B

LACTIPLANTIBACILLUS PLANTARUM EFFECTIVELY INHIBITING MULTI-DRUG-RESISTANT KLEBSIELLA PNEUMONIAE AND USE THEREOF

CROSS-REFERENCE TO RELATED APPLICATION

The present application claims priority from Chinese Patent Application No. 202311234569.X filed on Sep. 25, 2023, the contents of which are incorporated herein by reference in their entirety.

TECHNICAL FIELD

The present application relates to the field of food biotechnologies, and particularly to a *Lactiplantibacillus plantarum* strain which can effectively inhibit multi-drug-resistant *Klebsiella pneumoniae*.

BACKGROUND

As excellent probiotic candidate strains, Lactic acid bacteria can produce metabolites such as bacteriocin and organic acids, and has antagonistic activity against pathogenic bacteria and other probiotic characteristics, such as lowering blood glucose, improving intestinal barrier functions, regulating intestinal flora and improving the metabolism. Lactic acid bacteria, due to their safety and probiotic characteristics, are often used in yogurt fermentation, microecological preparation, and food additive industry. The products are safe, have unique flavor and probiotic function, and are particularly preferred by consumers.

Compared with adults and children over 1 year old, neonatal intestinal flora has the characteristics of simple structure, instability and great individual variability. The neonatal intestinal flora is very important for the digestion and absorption, growth and development, establishment of intestinal barrier and improvement of immune system. Profitable strains in the intestine, such as *Lactobacillus* and *Bifidobacterium*, can inhibit the growth of pathogenic bacteria, maintain the intestinal health, facilitate the digestion and absorption of nutrients in newborns, stimulate immune regulation and adjust the balance of flora. The potential pathogens can cause diarrhea, vomiting, allergies, indigestion and even gastroenteritis, seriously harming the health of newborns. *Klebsiella pneumoniae* is the most important class of bacteria in genus *Klebsiella*, family Enterobacteriaceae, which exists in human upper respiratory tract and intestine, and may cause serious diseases such as necrotizing enterocolitis (NEC), severe pneumonia, septicemia and purulent meningitis. In the process of disease treatment, the unreasonable use of antibiotics leads to the development of multi-drug-resistant *Klebsiella pneumoniae*, causing a great threat to human life and medical industry.

Currently, some studies prove that lactic acid bacteria can inhibit *Klebsiella pneumoniae*. For example, lactic acid bacteria K10 and K15 screened from cereals can destroy the biological membrane of *Klebsiella pneumoniae*; *Enterococcus faecalis* V583 produces lactic acid in a glucose-rich medium to change the pH value, thus affecting the growth of *Klebsiella pneumoniae*; and a novel cyclic dipeptide derived from *Lactiplantibacillus plantarum* MC39 can inhibit *Klebsiella pneumoniae* W8.

The Patent No. CN107312726A entitled *Lactiplantibacillus plantarum* strain ZN-3 and use thereof discloses that *Lactiplantibacillus plantarum* ZN-3 (deposited under CCTCC NO: M 2017286) has bacteriostatic effect on pathogenic bacteria of animal origin, including Gram-negative bacteria such as *Escherichia coli, Salmonella, Pasteurella multocida, Erysipelothrix rhusiopathiae, Haemophilus parasuis* and porcine infectious pleuropneumonia-induced bacteria; and Gram-positive bacteria such as *Streptococcus suis, Staphylococcus aureus*, and *Staphylococcus epidermidis*. Compared with antibiotics, it has a good bacteriostatic effect on pathogenic bacteria with strong drug resistance.

The Patent No. CN111394361A entitled *Brevibacillus laterosporus*, composition and use thereof discloses a *Brevibacillus laterosporus* strain B8, deposited under CGMCC No. 16337, can efficiently produce antibacterial peptides with inhibitory effects on Gram-positive bacteria (*Staphylococcus aureus*, drug-resistant *Staphylococcus aureus*, *Lacticaseibacillus casei*, *Lactiplantibacillus plantarum*, *Bacillus coagulans*, *Bacillus amyloliquefaciens*, and *Enterococcus*), Gram-negative bacteria (*Escherichia coli* and *Pneumobacillus*), and fungi (*Candida albicans* and *Aspergillus fumigatus*).

The Patent No. CN115851494A entitled *Lactiplantibacillus plantarum* strain NHE-LpE5 and use thereof discloses a *Lactiplantibacillus plantarum* strain NHE-LpE5, deposited under CGMCC NO. 24432. The lactic acid bacterium has broad-spectrum bactericidal activity, and can inhibit *Erysipelothrix rhusiopathiae, Pseudomonas aeruginosa, Klebsiella pneumoniae, Listeria ivanovii, Streptococcus pneumoniae*, enteropathogenic *Escherichia coli, Staphylococcus aureus, Salmonella typhi, Salmonella, Clostridium perfringens, Proteus penneri, Aeromonas hydrophila* and *Vibrio parahaemolyticus*.

The Patent No. CN116004430A entitled *Lactiplantibacillus plantarum* strain NHE-LpE9 and use thereof discloses use of *Lactiplantibacillus plantarum* strain NHE-LpE9 in the preparation of a broad-spectrum fungicide. The antibacterial spectrum of the broad-spectrum fungicide includes: *Erysipelothrix rhusiopathiae, Pseudomonas aeruginosa, Klebsiella pneumoniae, Listeria ivanovii, Streptococcus pneumoniae*, enteropathogenic *Escherichia coli, Staphylococcus aureus, Salmonella typhi, Salmonella, Clostridium perfringens, Proteus penneri, Aeromonas hydrophila* and *Vibrio parahaemolyticus*.

The Patent No. CN116083273A entitled *Lactiplantibacillus plantarum* strain NHE-LpE15 and use thereof discloses that *Lactiplantibacillus plantarum* NHE-LpE15 has broad-spectrum bactericidal activity and can inhibit many harmful strains.

SUMMARY

In view of the above technical problems, the present application provides a *Lactiplantibacillus plantarum* strain which can effectively inhibit multi-drug-resistant *Klebsiella pneumoniae*.

To solve the above technical problems, the present application provides a *Lactiplantibacillus plantarum* strain ZFM518, deposited under CCTCC NO: M 2022442.

ZFM518 is a *Lactiplantibacillus plantarum* strain effectively inhibiting multi-drug-resistant *Klebsiella pneumoniae*.

The present application also provides use of *Lactiplantibacillus plantarum* ZFM518 in the inhibition (effective inhibition) of multi-drug-resistant *Klebsiella pneumoniae*.

As an improvement in the use of the present application, the drug resistance refers to resistance to antibiotics such as penicillin, amoxicillin, cefuroxime, erythromycin, gentamycin, chloramphenicol and vancomycin.

As a further improvement in the use of the present application, it can inhibit (effectively inhibit) multi-drug-resistant *Klebsiella pneumoniae* ZFM4. The multi-drug-resistant *Klebsiella pneumoniae* ZFM4 is deposited under CCTCC NO: M 20221900.

The present application also provides a biologically pure culture of *Lactiplantibacillus plantarum* strain ZFM518 deposited under CCTCC NO: M 2022442, wherein said strain is isolated from fecal samples of newborns and exhibits inhibitory effects on multi-drug resistant *Klebsiella pneumoniae* ZFM4 deposited under CCTCC NO: M 20221900.

The present application also provides a composition including the biologically pure culture of *Lactiplantibacillus plantarum* strain ZFM518 and a pharmaceutically acceptable carrier. The composition may be formulated as an antibiotic or a probiotic.

The present application also provides a method of treating a subject infected by *Klebsiella pneumoniae* ZFM4 deposited under CCTCC NO: M 20221900, the method including a step of exposing an infected area of the subject to a composition comprising a therapeutically effective amount of a fermentation supernatant of a *Lactiplantibacillus plantarum* strain ZFM518 deposited under CCTCC NO: M 2022442.

The strain ZFM518 of the present application is *Lactiplantibacillus plantarum* ZFM518, deposited in China Center for Type Culture Collection (address: Wuhan University, Wuhan, China) under CCTCC NO: M 2022442, on Apr. 21, 2022. The deposit is based on the Budapest Treaty for the deposit of patent procedures. All restrictions imposed by the depositor on the availability to the public of the deposited *Lactiplantibacillus plantarum* ZFM518 will be irrevocably removed upon the granting of a patent.

Characteristics of *Lactiplantibacillus plantarum* ZFM518: The colony on MRS solid medium is round and convex, milky white, smooth and opaque, and has regular edges. Gram staining and microscopic examination show that the bacterium is gram-positive and rod-shaped.

The strain ZFM4 of the present application is *Klebsiella pneumoniae* ZFM4, deposited in China Center for Type Culture Collection (address: Wuhan University, Wuhan, China) under CCTCC NO: M 20221900, on Dec. 8, 2022. The deposit is based on the Budapest Treaty for the deposit of patent procedures. All restrictions imposed by the depositor on the availability to the public of the deposited *Klebsiella pneumoniae* ZFM4 will be irrevocably removed upon the granting of a patent.

Characteristics of *Klebsiella pneumoniae* ZFM4: The colony on MRS solid medium is large, oval, convex, and milky white, and has wet surface. Gram staining and microscopic examination show that the bacterium is Gram-negative, and short rod shaped.

The *Lactiplantibacillus plantarum* ZFM518 and *Klebsiella pneumoniae* ZFM4 are obtained as follows:

A process for obtaining the *Lactiplantibacillus plantarum* ZFM518 includes: collecting a feces sample from a healthy newborn, coating a feces suspension on a MRS solid medium containing calcium carbonate, anaerobically culturing at 37° C. for 72 hrs, picking up a single colony of lactic acid bacteria, culturing in a MRS liquid medium, identifying by 16S rDNA sequencing, to obtain *Lactiplantibacillus plantarum* ZFM518.

A process for obtaining the *Klebsiella pneumoniae* ZFM4 includes: collecting a feces sample from a newborn having necrotizing enterocolitis, coating a feces suspension on a MIAC solid medium, culturing at 37° C. for 24 hrs, picking up a single colony of *Klebsiella pneumoniae*, culturing in a LB liquid medium, and identifying by 16S rDNA sequencing, to obtain *Klebsiella pneumoniae* ZFM4.

*Lactiplantibacillus plantarum* ZFM518 has the following physical and chemical characteristics:
 (1) Hemolytic activity: *Lactiplantibacillus plantarum* ZFM518 shows y hemolysis, indicating that ZFM518 has good safety;
 (2) Temperature resistance: After ZFM518 is cultured at an optimum temperature of 37° C., the $OD_{600}$ is 3.08, and after culturing at 45° C., the $OD_{600}$ is 2.50, indicating that ZFM518 has good heat resistance;
 (3) Osmotic pressure resistance: When the concentration of NaCl is as high as 8%, the $OD_{600}$ is 0.49, indicating that ZFM518 has good osmotic pressure resistance;
 (4) Acid resistance: At pH 2.0, the survival rate of *Lactiplantibacillus plantarum* ZFM518 is 51.43%, and at pH 3.0, the survival rate can be up to 92.37%, indicating that ZFM518 has good acid resistance;
 (5) Viability in simulated gastrointestinal fluid: After being cultured in simulated gastric fluid environment for 2 hrs, the survival rate of *Lactiplantibacillus plantarum* ZFM518 is 63.72%; and after being cultured in simulated intestinal fluid environment for 2 hrs, the survival rate of *Lactiplantibacillus plantarum* ZFM518 can be up to 96.54%, and the survival rate is still 90.46% even after 4 hrs, indicating that ZFM518 has good adaptability to the gastrointestinal environment.
 (6) Folic acid production capacity: The folic acid content produced is 3.32 ng/mL, indicating that ZFM518 has good probiotic characteristics;
 (7) Blood glucose lowering ability: The rate of inhibition on α-glucosidase is 80.48±1.60%, indicating that ZFM518 has good blood glucose lowering ability.

Therefore, *Lactiplantibacillus plantarum* ZFM518 has safety, probiotic characteristics and high environmental adaptability.

The virulence, drug resistance, resistance gene and in-vitro drug resistance of *Klebsiella pneumoniae* ZFM4 are studied. The results are as follows:

As determined by the genome sequencing of *Klebsiella pneumoniae* ZFM4, ZFM4 has 419 virulence genes, involving 155 virulence factors, including not only lipopolysaccharide, adhesive fimbriae, capsule, ironophore system, and other common virulence factors found in *Klebsiella pneumoniae*, but also PuI, T3SS, T4SS, T6SS and other transport systems, and nutrient metabolism factors such as heme synthesis and trehalose cycle transporter. These virulence factors help *Klebsiella pneumoniae* ZFM4 escape from the immune phagocytosis of the host, are attached to, colonized in and invade the host, and finally induce the host to produce inflammatory reaction.

*Klebsiella pneumoniae* ZFM4 has 28 drug resistance genes and 141 resistance genes, and is predicted to be resistant to many antibiotics such as aminoglycosides, β-lactams, macrolides and quinolones. The antibiotic resistance of *Klebsiella pneumoniae* ZFM4 is evaluated by disk diffusion method. It is found that the strain is resistant to 7 antibiotics, including penicillin, amoxicillin, cefuroxime, erythromycin, gentamycin, chloramphenicol and vancomycin, has strong antibiotic resistance, and multiple drug resistance. This is consistent with the results of drug resistance and resistance gene analysis.

The bacteriostatic effect of *Lactiplantibacillus plantarum* ZFM518 on *Klebsiella pneumoniae* ZFM4 is determined by agar diffusion assay in Oxford cup. The fermentation supernatant of *Lactiplantibacillus plantarum* ZFM518 is incubated at 37° C. for 18 hrs in an Oxford cup hole formed of LB semi-solid culture medium (1%, v/v) containing *Klebsiella pneumoniae* ZFM4, and the diameter of a transparent circle is measured. The result shows that the diameter of the bacteriostatic circle is 20.76±1.09 mm, showing good bacteriostatic activity.

Compared with related art, the present application has the following technical advantages.

1. Strains are respectively screen from feces of a healthy newborn and a newborn having necrotizing enterocolitis, to obtain a novel *Lactiplantibacillus plantarum* strain ZFM518 and a novel *Klebsiella pneumoniae* strain ZFM4.

2. *Lactiplantibacillus plantarum* ZFM518 has safety, probiotic characteristics and high adaptability to gastrointestinal environment, and effectively inhibits multi-drug-resistant *Klebsiella pneumonia* ZFM4.

3. *Lactiplantibacillus plantarum* ZFM518 obtained in the present application has the potential to be applied to functional products, antibiotic substitute products and other products.

Therefore, *Lactiplantibacillus plantarum* and *Klebsiella pneumoniae* are respectively screened from feces of a healthy newborn and feces of a newborn suffering from necrotizing enterocolitis in the present application. The osmotic pressure resistance, low pH resistance, resistance to simulated gastrointestinal fluid, folic acid production and blood glucose lowering ability of *Lactiplantibacillus plantarum* are tested in vitro to explore its physiological characteristics. By testing the hemolytic activity, the safety is confirmed. The inhibition of this strain on *Klebsiella pneumoniae* is investigated. By the virulence gene and resistance gene analysis and the drug sensitivity experiment, the drug resistance of *Klebsiella pneumoniae* is investigated. The screening of lactic acid bacteria with probiotic potential and development of antibiotic substitute products in the present application have great significance.

4. The impact of *Lactiplantibacillus plantarum* ZFM518 on the neonatal microbial composition via in vitro human intestinal flora simulation system. The findings revealed that *Lactiplantibacillus plantarum* ZFM518 administration significantly reduced the relative abundance of *Clostridium_sensu_stricto_1* and *Enterococcus*, while increasing the prevalence of *Bifidobacterium, Weisella, Bacteroides,* and *Lactobacillus*. These changes indicate a beneficial effect of *Lactiplantibacillus plantarum* ZFM518 on the structure of the intestinal microbiota.

5. After non-targeted metabolic analysis, it was found that amino acids and their derivatives accounted for approximately 35% of the differential metabolites in fecal fermentation samples. Following the intervention of *Lactiplantibacillus plantarum* ZFM518, the metabolites in the sample group of children with NEC were significantly increased. Valine was up-regulated by 238.62 times, L-tryptophan by 50.22 times, and there was a notable upregulation for organic acids such as butyric acid, lactic acid, and L-phenyllactic acid.

BRIEF DESCRIPTION OF THE DRAWINGS

The specific embodiments of the present application will be further described in detail with reference to the accompanying drawings.

where (A) Distribution at the phylun level, and (B) Distribution at the genus level.

Figure 7:
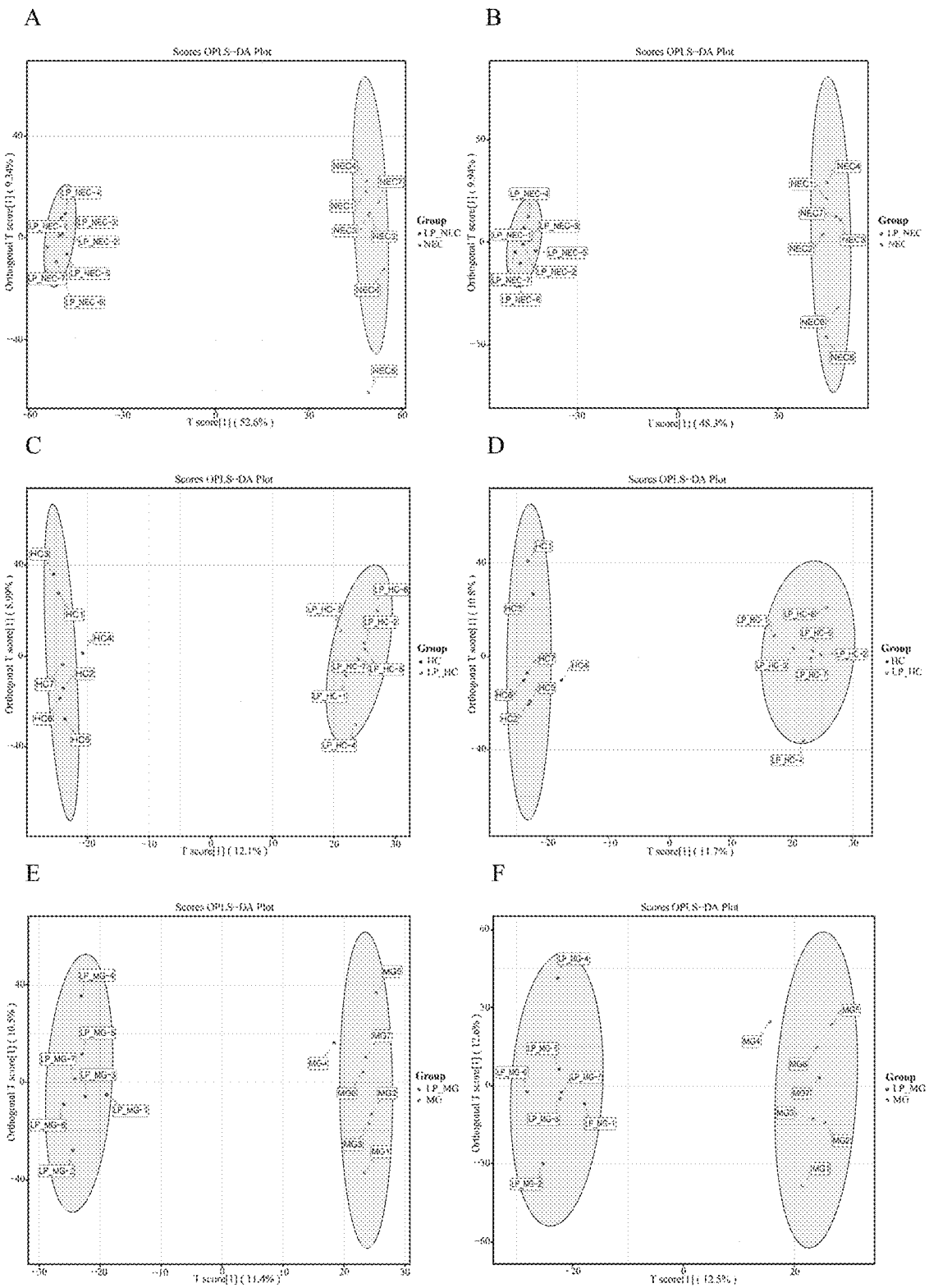

FIG. 7 shows the OPLS-DA score chart of metabolites.

where (A) and (B): NEC group and LP_NEC group under positive and negative ions; (C) and (D): HC group and LP_HC group under positive and negative ions; (E) and (F): MG group and LP_MG group under positive and negative ions.

Figure 8:
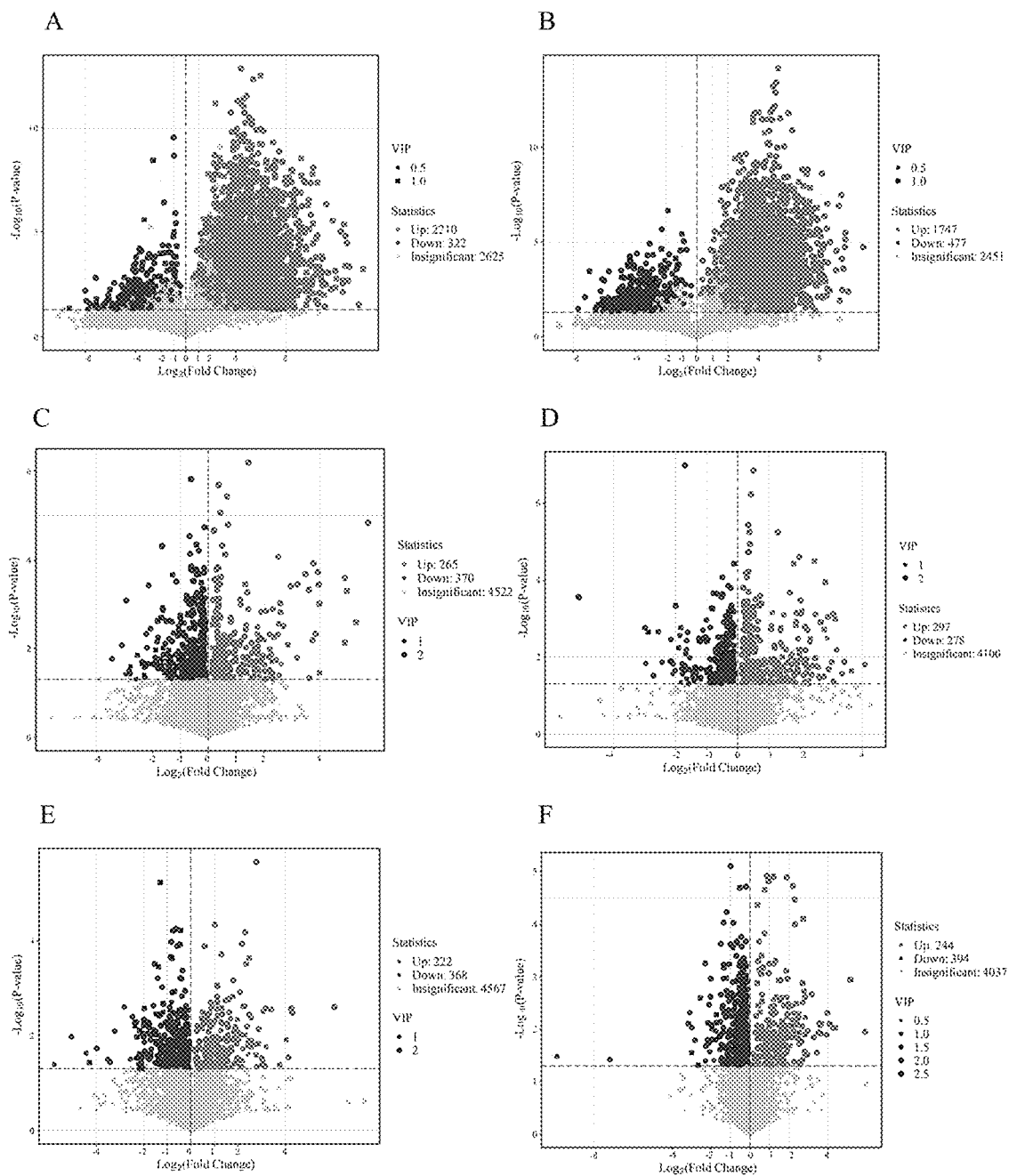

FIG. 8 shows the volcano map of metabolites.

where (A) and (B): NEC group and LP_NEC group under positive and negative ions; (C) and (D): HC group and LP_HC group under positive and negative ions; (E) and (F): MG group and LP_MG group.

DETAILED DESCRIPTION

The present application will be further described below with reference to specific embodiments. However, the protection scope of the present application is not limited thereto.

Example 1: Collection and Storage of Neonatal Fecal Samples

The fecal samples of healthy newborns and newborns having necrotizing enterocolitis were derived from the Obstetrics and Gynecology Hospital affiliated to School of Medicine, Zhejiang University. After the newborn excreted feces, the fecal samples were collected by using a disposable aseptic sampler to avoid urine pollution and transferred at a low temperature of 0-4° C.

Inclusion criteria of feces from newborns with necrotizing enterocolitis: (1) Clinical diagnostic criteria of NEC: Newborns in Stage I lack specific symptoms and are suspicious. Inflammatory indexes of newborns in Stage II rise, frequently accompanied by symptoms of intestinal pneumatosis and peritonitis. In Stage III, the condition is deteriorated seriously, symptoms of intestinal perforation, panperitonitis and intestinal necrosis are developed. (2) Exclusion criteria: Newborns with abnormal intestinal development.

Standards for collecting fecal samples of healthy newborns: The feeding mode, delivery mode, and body mass index of healthy newborns match those of newborns with necrotizing enterocolitis, and no antibiotics and microecological agents are used before and after sample collection; the newborn mothers do not suffer from chorioamnionitis; the intestinal development is normal and there is no disease.

Example 2: Isolation and Identification of Strains

Isolation of lactic acid bacteria: Under aseptic conditions, 0.5 g of fresh healthy newborn's feces was diluted with 5 mL of sterilized PBS buffer, and fully shaken until uniform. A fecal suspension was obtained by filtration with a sterilized metal screen. 100 μL was coated on MRS solid medium containing calcium carbonate (at a concentration of 1.5%), and anaerobically cultured at 37° C. for 72 hrs. The milky white single colony with a calcium dissolving circle was picked into a MRS liquid medium. Then, the strain was purified 2 times by streaking MRS solid medium. After culture in the liquid medium, the morphological characteristics of lactic acid bacteria were preliminarily identified following the method provided by the Gram staining kit (purchased from Qingdao Haibo Biotechnology Co., Ltd.).

Isolation of *Klebsiella pneumoniae*: The fecal samples of newborns with necrotizing enterocolitis were pretreated in the same way as that for the feces of healthy newborns, coated on MIAC solid medium and cultured at 37° C. for 24 hrs. The rose red single colony was picked into LB liquid medium. The strain was purified 2 times by streaking. After culture in the liquid medium, the strain was deposited.

The strains were preliminarily identified as a strain of lactic acid bacteria and a strain of *Klebsiella pneumoniae*. At a low temperature, they were shipped to Sangon Biotech (Shanghai) Co., Ltd. and identified by 16S rDNA sequencing. Finally, a *Lactiplantibacillus plantarum* strain ZFM518 and a *Klebsiella pneumoniae* strain ZFM4 were obtained and deposited in China Center for Type Culture Collection under CCTCC NO: M 2022442 and CCTCC NO: M 20221900.

Strain ZFM518 is *Lactiplantibacillus plantarum* ZFM518, deposited in China Center for Type Culture Collection (address: Wuhan University, Wuhan, China) under CCTCC NO: M 2022442, on Apr. 21, 2022.

Strain ZFM4 is *Klebsiella pneumoniae* ZFM4, deposited in China Center for Type Culture Collection (address: Wuhan University, Wuhan, China) under CCTCC NO: M 20221900, on Dec. 8, 2022.

Example 3: Study on Physical and Chemical Characteristics and Probiotic Performance of *Lactiplantibacillus plantarum* ZFM518

(1) Strain Culture and Sample Preparation:

*Lactiplantibacillus plantarum* ZFM518 stored in a freezer at −80° C. was taken out, streaked on MRS solid medium, and anaerobically cultured at 37° C. for 48 hrs. Then, the single colony was picked into 10 mL of MRS liquid medium, and anaerobically cultured at 37° C. for 12 hrs, to obtain a first-generation bacterial culture. 2% of the first-generation bacterial culture was inoculated into 10 mL of MRS liquid medium, anaerobically cultured at 37° C. for 24 hrs, and centrifuged at 4500×g and 4° C. for 10 min. The bacterial precipitation was discarded to finally obtain a fermentation supernatant of ZFM518.

*Klebsiella pneumoniae* ZFM4 stored in a freezer at −80° C. was taken out, streaked on LB solid medium, and aerobically cultured at 37° C. for 24 hrs. Then, the single colony was picked into 10 mL of LB liquid medium, and aerobically cultured at 37° C. for 12 hrs, to obtain a first-generation bacterial culture. 2% of the first-generation bacterial culture was inoculated into 10 mL of LB liquid medium, and aerobically cultured at 37° C. for 12 hrs, to finally obtain a second-generation bacterial culture of ZFM4.

(2) Determination of Hemolytic Activity:

There are mainly three types of strains: α hemolytic, β hemolytic and γ hemolytic, showing green, transparent and hemolytic-free areas around the strains. The strain showing γ hemolysis is considered to be safe. The hemolytic activity of ZFM518 was determined by Columbia agar containing 5% (w/v) sheep blood, and the plate was cultured anaerobically at 37° C. for 48 hrs. After culture, the hemolytic activity of ZFM518 was evaluated according to the presence of a hemolytic region in the culture medium around the colony.

*Lactiplantibacillus plantarum* ZFM518 shows γ hemolysis, indicating that ZFM518 has good safety.

Figure 1:
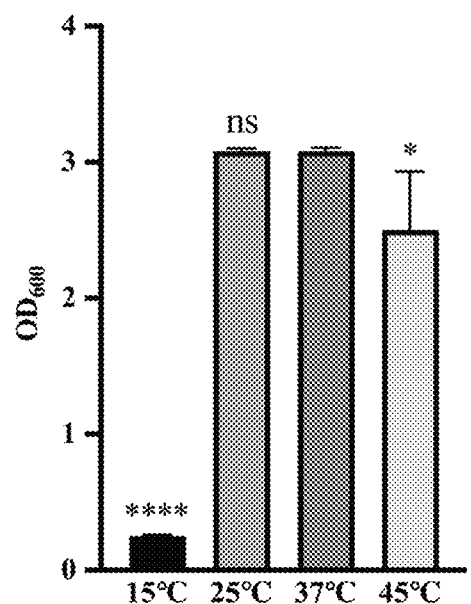
FIG. 1 shows the temperature resistance of *Lactiplantibacillus plantarum* ZFM518.

(3) Determination of Temperature Resistance:

The absorbance ($OD_{600}$) of the strain at 600 nm can reflect the growth state of the strain. The greater the $OD_{600}$ is, the greater the cell concentration of the strain will be. $OD_{600}$ of the ZFM518 suspension obtained in Step (1) was adjusted to 1, and 1% was inoculated in MRS liquid medium, and anaerobically cultured at 15° C., 25° C. 37° C. and 45° C. for 24 hrs. After the culture, the absorbance at 600 nm was determined, as shown in FIG. 1.

After ZFM518 is cultured at an optimum temperature of 37° C., the $OD_{600}$ is 3.08, after culturing at 45° C., the $OD_{600}$ is 2.50, indicating that ZFM518 has good heat resistance.

Figure 2:
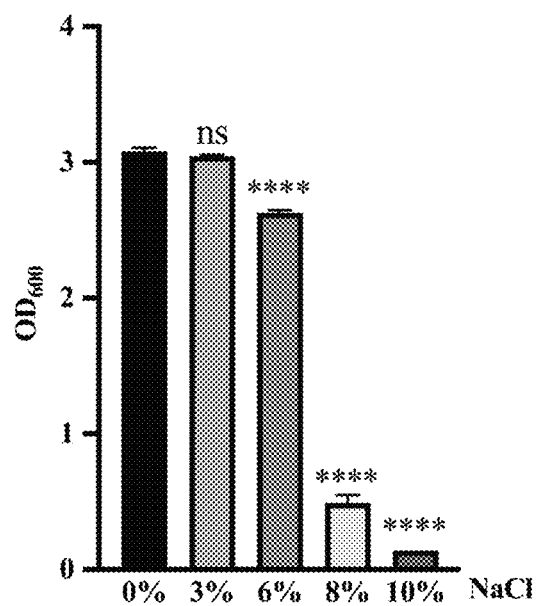
FIG. 2 shows the osmotic pressure resistance of *Lactiplantibacillus plantarum* ZFM518.

(4) Determination of Osmotic Pressure Resistance:

The same bacterial suspension of ZFM518 in Step (3) was inoculated in an amount of 1% in MRS liquid culture medium containing 0%, 3%, 6%, 8% or 10% sodium chloride respectively, and anaerobically cultured for 24 hrs in a constant-temperature incubator at 37° C. The absorbance of the bacterial suspension was measured at 600 nm, as shown in FIG. 2.

When the concentration of NaCl is as high as 8%, the $OD_{600}$ is 0.49, indicating that ZFM518 has good osmotic pressure resistance.

(5) Determination of Acid Resistance:

The bacterial suspension of ZFM518 in Step (1) was adjusted to have a viable cell count of $10^8$ CFU/mL.

Figure 3:
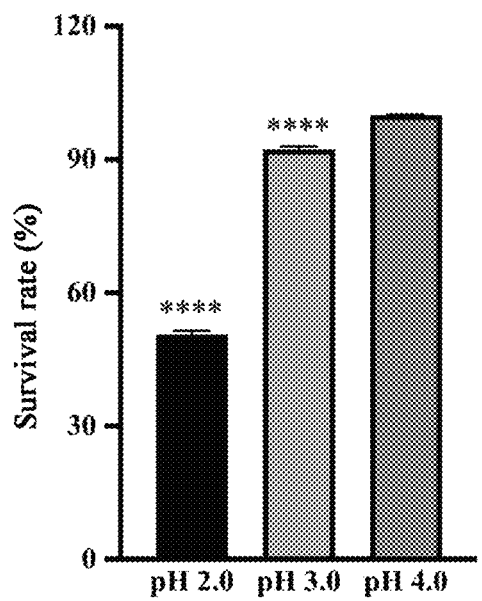
FIG. 3 shows the acid resistance of *Lactiplantibacillus plantarum* ZFM518.

The PBS buffer was adjusted with 1 mol/L HCl to pH 2.0, 3.0 or 4.0. 500 μL of the bacterial suspension was taken in 4.5 mL of PBS buffer with different pH, and then anaerobically cultured in an incubator at 37° C. Samples were taken at 0 h and 2 h, respectively, the bacteria were counted by spread plate method. The survival rate of ZFM518 at different pH values was calculated according to the following formula, as shown in FIG. 3.

Survival rate calculation formula: $S=(\text{Log } N_1)/(\text{Log } N_0)$, where: S represents the survival rate of ZFM518, %; $N_0$ is the viable cell count at 0 h, CFU/mL; $N_1$ is the viable cell count at 2 h, CFU/mL.

At pH 2.0, the survival rate of *Lactiplantibacillus plantarum* ZFM518 is 51.43%, and at pH 3.0, the survival rate can be up to 92.37%, indicating that ZFM518 has good acid resistance.

Figure 4:
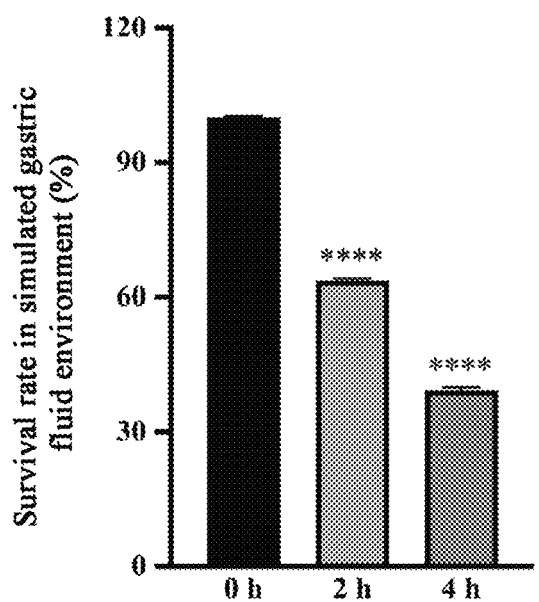
FIG. 4 shows the resistance of *Lactiplantibacillus plantarum* ZFM518 to simulated gastric fluid.

(6) Determination of Resistance to Simulated Intestinal Fluid:

500 μL of the same bacterial suspension (viable cell count $10^8$ CFU/mL) in Step (5) was inoculated into 4.5 mL of simulated gastric fluid (0.3 g of pepsin was taken in PBS q.s. to 100 mL, adjusted to pH 2.5, fully vibrated, and then filtered through 0.22 μm filter membrane), mixed uniformly, and anaerobically cultured at 37° C. At 0 h, 2 h and 4 h, the cells were counted by spread plate method, and the survival rate of ZFM518 in simulated gastric fluid was calculated according to the following formula, as shown in FIG. 4.

Figure 5:
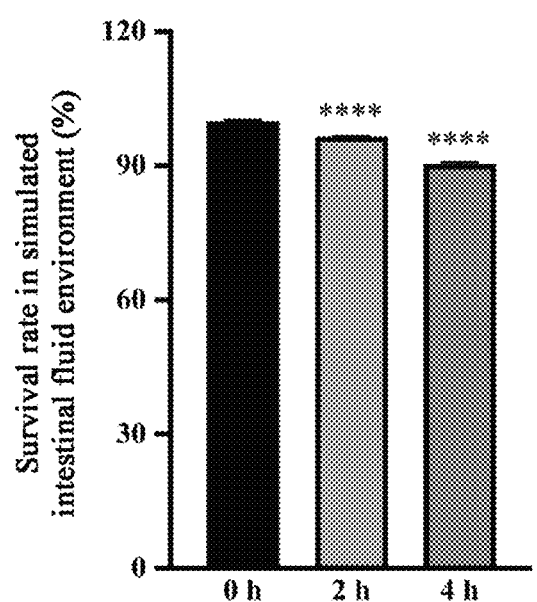
FIG. 5 shows the resistance of *Lactiplantibacillus plantarum* ZFM518 to simulated intestinal fluid.

500 μL of the same bacterial suspension in Step (5) was inoculated into 4.5 mL of simulated intestinal fluid (0.1 g of trypsin and 0.3 g of bile salt were taken in PBS q.s. to 100 mL, adjusted to pH 7.8, fully vibrated, and then filtered through 0.22 μm filter membrane), mixed uniformly, and anaerobically cultured at 37° C. At 0 h, 2 h and 4 h, the cells were counted by spread plate method, and the survival rate of ZFM518 in simulated intestinal fluid was calculated according to the following formula, as shown in FIG. 5.

Survival rate in simulated gastrointestinal fluid
$$S=(\text{Log } N_1)/(\text{Log } N_0),$$

where: S represents the survival rate of ZFM518, %; $N_0$ is the viable cell count at 0 h, CFU/mL; $N_1$ is the viable cell count at 2 h or 4 h, CFU/mL.

After being cultured in simulated gastric fluid for 2 hrs, the survival rate of *Lactiplantibacillus plantarum* ZFM518 is 63.72%; and after being cultured in simulated intestinal fluid for 2 hrs, the survival rate of *Lactiplantibacillus plantarum* ZFM518 can be up to 96.54%, and the survival rate is still 90.46% even after 4 hrs, indicating that ZFM518 has good adaptability to the gastrointestinal environment.

(7) Determination of Folic Acid Content Produced:

Using an ELISA kit, the folic acid content was detected by the mutual binding of antigen and antibody. The specific steps were as follows. The same bacterial suspension in Step (5) was inoculated in an amount of 2% (v/v) into a culture medium for folic acid determination, and anaerobically cultured at 37° C. for 24 hrs. 500 μL of the bacterial culture was mixed with 500 μL of PBS buffer, centrifuged (6000×g, 4° C., 10 min), and washed with a folic acid buffer, to prepare a bacterial suspension. The bacterial suspension was allowed to stand in a water bath at 100° C., and then immediately in an ice bath to destroy the cell wall, centrifuged again under the same conditions to obtain a supernatant. The supernatant was added and treated with 2.5% (v/v) chicken pancreatin at 37° C. for 2 hrs. Then it was added to a well of an ELISA plate coated with a folic acid antibody, and incubated at 37° C. for 30 min. Then an enzyme-labeled detection reagent and a developing agent were added, and the absorbance at 450 nm was measured. According to a standard curve of the folic acid standard, the folic acid content produced by ZFM518 is 3.32 ng/mL.

(8) Determination of blood glucose lowering ability: According to the inhibition rate of cell-free supernatant (CFS) and intracellular cell-free extract (CFE) of ZFM518 on α-glucosidase which can decompose carbohydrates to produce blood glucose, the blood glucose lowering ability was determined. The specific steps were as follows. The same bacterial suspension in Step (3) (12000×g, 4° C. 15 min) was centrifuged, and the supernatant was collected and filtered through a 0.22 μm microporous filter membrane to obtain CFS. The bacterial suspension was mixed uniformly, ultrasonically disrupted in an ice bath for 30 min, and centrifuged under the same conditions. The supernatant was collected and filtered through a filter membrane, to obtain CFE. In a 210 μL reaction system in a 96-well plate, 50 μL of PBS and 50 μL of PNPG (4-nitrophenol-α-D-glucopyranoside) were added and incubated at 37° C. for 10 min. Then 30 μL of α-glucosidase solution was added to continue the reaction at 37° C. for 30 min. Finally, 50 μL of $Na_2CO_3$ solution was added to terminate the reaction. The absorbance at 405 nm was determined. The α-glucosidase inhibition rate of commercial strain *Lacticaseibacillus rhamnosus* GG, which was proved to have blood glucose lowering effect, was used as the control. PBS was used as the blank control of α-glucosidase solution and the sample to be tested. The α-glucosidase inhibition rate was calculated by a formula below. The inhibition rate of CFE of ZFM518 on α-glucosidase is 42.95±1.13%, and the inhibition rate of CFE on α-glucosidase is 80.48±1.60%; indicating that ZFM518 has good blood glucose lowering ability.

$$\alpha\text{-glucosidase inhibition rate (\%)} = \left(1 - \frac{A-B}{C-D}\right) \times 100,$$

where: A is the sample group, containing the sample solution and the α-glucosidase solution; B is the sample blank group, containing the sample solution but not the α-glucosidase solution; C is the control group, containing the α-glucosidase solution, but not the sample solution; and D is the blank group, containing no sample solution and no α-glucosidase solution.

Example 4: Virulence Gene, Drug-Resistant Gene, and Drug Resistance Study of *Klebsiella pneumoniae* ZFM4

*Klebsiella pneumoniae* ZFM4 was sequenced by Novogene Bioinformation Technology Co., Ltd, to obtain the complete genome sequence. The sequence was compared with VFDB and ARDB databases by DIAMOND software, to obtain the functional annotation information of the virulence and drug resistance genes. The resistance gene information was obtained by comparing with CARD database by RGI software. The analysis results show that:

ZFM4 has up to 419 virulence genes, involving 155 virulence factors, including not only lipopolysaccharide (LPS), adhesive fimbriae, capsule, ironophore system, and other virulence factors frequently found in relevant research of *Klebsiella pneumoniae*, but also PuI, T3SS, T4SS, T6SS and other transport systems, and nutrient metabolism factors such as heme synthesis and trehalose cycle transporter. These virulence factors help to inhibit serum complement protein, prevent the host from phagocytizing ZFM4 to increase its spread and survival ability, so that ZFM4 is attached to and colonized in the host to form a biofilm and invade the host, and finally induce the host to produce inflammatory reaction.

ZFM4 has 28 drug-resistant genes, and is predicted to be resistant to 27 antibiotics, for example, aminoglycosides, including gentamicin, tobramycin, fosfomycin, netilmicin and isepamicin; β-lactams, including penicillin, cephalosporin and ceftizoxime; quinolones, including fluoroquinolone, enoxacin and norfloxacin; and chloramphenicols, tetracyclines, macrolides, glycylcyclines and other antibiotics.

ZFM4 has 141 drug-resistant genes. The results of functional annotation are mainly related to antibiotic inactivating enzymes, drug-resistant molecular pathways, compounds regulating antibiotic excretion, phenol resistance, and changes of cell wall charge, etc. The result predicts that ZFM4 is resistant to antibiotics such as aminoglycosides, β-lactams, macrolides, tetracyclines, polypeptides, chloramphenicols, quinolones, sulfonamides, polyphosphates and rifamycins, which is consistent with the results of drug-resistant gene analysis, showing multiple drug resistance.

The antibiotic susceptibility test disk was purchased from Hangzhou Microbial Reagent Co., Ltd., including amoxicillin, cefuroxime, gentamycin, erythromycin, vancomycin, tetracycline, penicillin, ciprofloxacin, streptomycin, and chloramphenicol.

The antibiotic resistance of *Klebsiella pneumoniae* ZFM4 was evaluated by disk diffusion method. 100 μL of the second-generation bacterial culture of *Klebsiella pneumoniae* ZFM4 was coated on LB solid medium and the antibiotic susceptibility test disk was placed on the plate. After aerobically incubation at 37° C. for 48 hrs, the diameter of the inhibition zone was measured. The antibiotic resistance of the strain was evaluated according to different evaluation criteria, as shown in the following table. The results show that ZFM4 is resistant to penicillin, amoxicillin, cefuroxime, erythromycin, gentamycin, chloramphenicol and vancomycin (five categories in total), and moderately resistant to streptomycin and ciprofloxacin. That is, *Klebsiella pneumoniae* ZFM4 had multiple drug resistance.

tion on drug-resistant *Klebsiella pneumoniae* ZFM4. *Lactiplantibacillus plantarum* ZN-3 only has inhibitory effect on *Escherichia coli* resistant to penicillin, ampicillinum, gentamicin and kanamycin and *Staphylococcus aureus* resistant to penicillin, doxycycline, ofloxacin and ciprofloxacin. *Brevibacterium laterosporus* B8 can only inhibit *Enterococcus* resistant to vancomycin and *Staphylococcus aureus* resistant to methicillin.

TABLE 1

Drug resistance of ZFM4 to antibiotics

| Categories of antibiotics | Name | Specification (μg/tablet) | Susceptibility (S) | Evaluation criteria of drug resistance (mm) | | Drug resistancee evaluation result |
|---|---|---|---|---|---|---|
| | | | | Intermediate resistance (I) | resistancee (R) | |
| β-lactams | Penicillin | 10 | ≥18 | 14-18 | ≤14 | R |
| β-lactams | Amoxicillin | 25 | ≥18 | 13-18 | ≤13 | R |
| β-lactams | Cefuroxime, | 30 | ≥15 | 10-15 | ≤10 | R |
| Macrolides | Erythromycin | 15 | ≥23 | 13-23 | ≤13 | R |
| Aminoglycosides | Streptomycin | 10 | ≥15 | 11-15 | ≤11 | I |
| Aminoglycosides | Gentamicin | 10 | ≥15 | 12-15 | ≤12 | R |
| Tetracyclines | Tetracycline | 30 | ≥15 | 11-15 | ≤11 | S |
| Chloramphenicols | Chloramphenicol | 30 | ≥18 | 12-18 | ≤12 | R |
| Polypeptides | Vancomycin | 30 | ≥17 | 14-17 | ≤14 | R |
| Quinolones | Ciprofloxacin | 5 | ≥21 | 15-21 | ≤15 | I |

Example 5: Inhibition of *Lactiplantibacillus plantarum* ZFM518 on *Klebsiella pneumoniae* ZFM4

*Lactiplantibacillus plantarum* ZFM518 was prepared according to the method described in Example 3. *Lactiplantibacillus plantarum* ZFM518 stored in a freezer at −80° C. was taken out, streaked on MRS solid medium, and anaerobically cultured at 37° C. for 48 hrs. Then, the single colony was picked into 10 mL of MRS liquid medium, and anaerobically cultured at 37° C. for 12 hrs, to obtain a first-generation bacterial culture. 2% of the first-generation bacterial culture was inoculated into 10 mL of MRS liquid medium, anaerobically cultured at 37° C. for 24 hrs, and centrifuged at 4500×g and 4° C. for 10 min. The bacterial precipitation was discarded to finally obtain a fermentation supernatant of ZFM518.

*Klebsiella pneumoniae* ZFM4 was cultured following a method as described in (1) of Example 3. The second-generation bacterial culture of ZFM4 was adjusted to $10^6$ CFU/mL, and 150 μL was inoculated into 15 mL of LB semi-solid culture medium, and mixed uniformly. It was poured into a culture plate where the Oxford cup was placed, and the Oxford cup was pulled out after solidification. 100 μL of fermentation supernatant of ZFM518 ($10^9$ CFU/mL) was added to the hole, transferred to an incubator at 37° C., and aerobically incubated for 18 hrs, and the diameter of a transparent circle was measured. The results show that *Lactiplantibacillus plantarum* ZFM518 has good antibacterial activity against multi-drug-resistant *Klebsiella pneumoniae* ZFM4, and the diameter of the inhibitory zone reaches 20.76±1.09 mm, indicating that ZFM518 has the potential to replace antibiotics.

It is to be understood that *Lactiplantibacillus plantarum* NHE-LpE5, *Lactiplantibacillus plantarum* NHE-LpE9, and *Lactiplantibacillus plantarum* NHE-LpE15 only have inhibition on usual *Klebsiella pneumoniae*, and have no inhibi- Example 6: The Effect of *Lactiplantibacillus plantarum* ZFM518 on the Diversity of Fecal Microbiota 0.5 g feces of healthy or neonates with enteritis was mixed with 4.5 mL of physiological saline (PBS) and filtered. There were divided into 6 groups, labeled HC, LP_HC, MG, LP_MG, NEC and LP_NEC, respectively. The HC, MG and NEC group were inoculated with 500 μL of healthy feces, healthy feces with *Klebsiella pneumoniae* ZFM4 ($10^6$ CFU/mL), and enteritis neonatal feces into 5 mL of YCFA broth, respectively. After the same preparation, LP_HC, LP_MG and LP_NEC group were added with *Lactiplantibacillus plantarum* ZFM518 ($10^9$ CFU/mL). The fecal fermentation liquid was collected for bacterial sequencing and metabolomic analysis.

Figure 6:
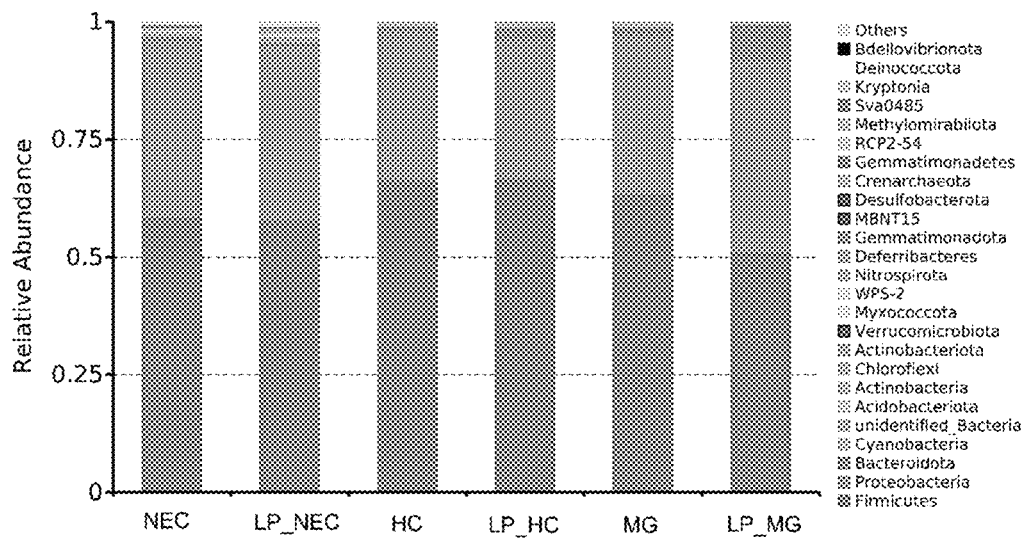
FIG. 6 shows the bacterial distribution at the phylun and genus level of intestinal microbiota.
Figure 6:
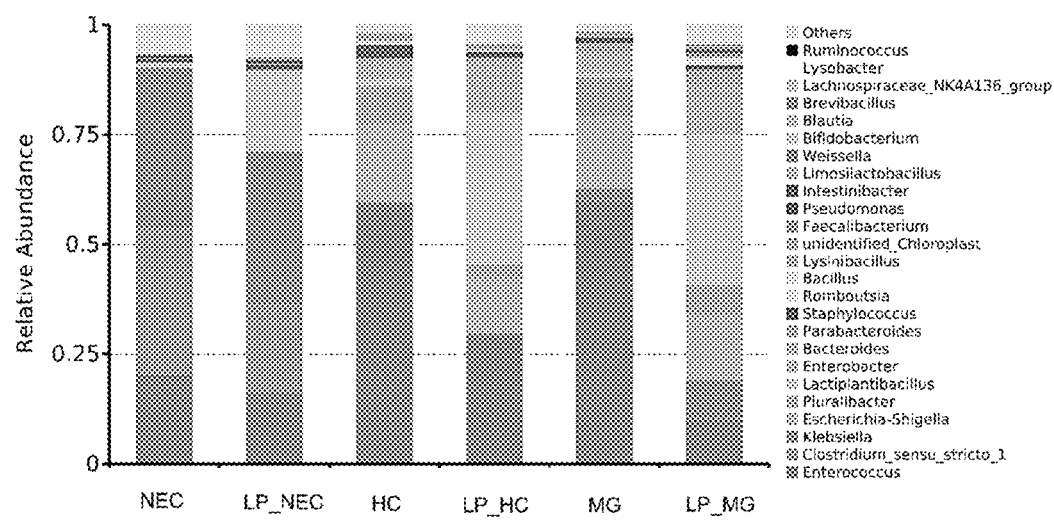

The top three in all groups at the phylum level are Firmicutes, Proteobacteria and Bacteroidetes (FIG. 6). The top three genera in NEC group abundance ranking are *Enterococcus*, *Clostridium_sensu_stricto*_1 and *Klebsiella*. After the intervention of *L. plantarum* ZFM518, the abundance of *Clostridium_sensu_stricto*_1 in LP_NEC group decreased and the abundance of *Lactiplantibacillus* increased. In HC group, *Enterococcus* and *Escherichia Shigella* were dominant, after the intervention of *Lactiplantibacillus plantarum* ZFM518, the abundance of *Lactobacillus* in LP_HC group was significantly increased, and the abundance of *Enterobacter* was increased. After the intervention of *Lactiplantibacillus plantarum* ZFM518, the abundance of *Klebsiella pneumoniae* did not decrease significantly. the abundance of *Bifidobacterium* in LP_MG group is higher than that in MG group, indicating that *Lactiplantibacillus plantarum* ZFM518 does have a regulating effect on gut microbiota. The relative abundance of *Clostridium_sensu_stricto*_1 and *Klebsiella* in NEC group was significantly higher than that of HC group. The abundance of *Klebsiella* species in the MG group was significantly higher than that in the HC group, indicating that the in vitro model of the MG group was successful.

Example 7: The Effect of *Lactiplantibacillus plantarum* ZFM518 on Fecal Microbial Metabolism From the results of principal component analysis, it can be seen that the clustering effect of metabolites within each group is very good, however, except for the NEC group and LP_NEC group, there were no significant differences in metabolites between the HC group and LP_HC group, as well as between the MG groups and LP_MG group (FIG. 7). From the results of OPLS-DA, in positive and negative ion modes, the difference between NEC group and LP_NEC group is significant, and the difference in NEC group is greater than that in LP_NEC group, indicating that *Lactiplantibacillus plantarum* ZFM518 has a significant regulatory effect on gut microbiota metabolism of NEC newborn infants. The interpretation rate of principal component were 12.1% and 11.7% in the HC group and LP_HC group, while in the MG group and LP_MG group were 11.4% and 12.5%. It showed that *Lactiplantibacillus plantarum* ZFM518 had similar metabolic regulation on gut microbiota in HC group and MG group.

By combining T-test, multiple change method, and OPLS-DA analysis method, differential metabolites between groups were identified, and the results were presented in the form of volcanic maps (FIG. 8). In the positive ion mode, the significantly upregulated metabolites of the total differential metabolites in the LP_HC group, LP_NEC group, and LP_MG group accounted for 41.73%, 87.28%, and 37.63%, the significantly downregulated metabolites accounted for 58.27%, 12.72%, and 62.37% respectively. In the negative ion mode, the significantly upregulated metabolites of the total differential metabolites in the LP_HC group, LP_NEC group, and LP_MG group accounted for 51.65%, 78.55%, and 38.24%, the significantly downregulated metabolites accounted for 48.35%, 22.45%, and 62.76% respectively. Above all, *Lactiplantibacillus plantarum* ZFM518 has a significant regulatory effect on the NEC group, with approximately 80% of metabolites showing an upward trend and 20% of metabolites showing a downward trend. However, the regulatory trend of *Lactiplantibacillus plantarum* ZFM518 on HC group and MG group is consistent.

Based on $P<0.05$, FC value $\geq 2$ or FC value $\leq 0$, and VIP$\geq 1$, the differential metabolites between groups were screened. In regulating amino acid metabolism, the content of valine in LP_HC group was higher than that in HC group. Compared with NEC group, tryptophan, tryptophan enzyme and valine derivatives were up-regulated in LP_NEC group. Tryptophan in LP_NEC group was up-regulated, indicating that *Lactiplantibacillus plantarum* had a positive regulatory effect. Compared with MG group, valine and phenylalanine were up-regulated in LP_MG group. It is worth mentioning that after the intervention of *Lactiplantibacillus plantarum* ZFM518, the uric acid in the LP_HC group, LP_NEC group, and LP_MG group showed a downward trend. In the regulation of amine substances, glutathione and nicotinamide were up-regulated in LP_NEC group compared with NEC group. The LP_NEC group showed upregulation of butyric acid, lactate, 6-hydroxynicotinic acid, and phenyllactate compared to the NEC group. 6-hydroxynicotinic acid is an important raw material for the synthesis of vitamin A. The LP_MG group showed an upregulation of phenyllactate compared to the MG group.

TABLE 2

| Differential metabolites | High abundant group | Ion mode | VIP | P-value | Fold_Change |
|---|---|---|---|---|---|
| Valine | LP_HC | Positive | 1.41 | 0.04 | 2.62 |
|  | LP_NEC | Positive | 1.32 | 0.01 | 239.62 |
|  | LP_MG | Positive | 1.21 | 0.02 | 2.43 |
| L-valine | LP_NEC | Positive | 1.34 | 0.00 | 24.62 |
| L-tryptophan | LP_NEC | Negative | 1.38 | 0.01 | 51.22 |
| D-tryptophan | LP_NEC | Negative | 1.26 | 0.00 | 20.55 |
| Tryptophanase | LP_NEC | Negative | 1.15 | 0.00 | 11.16 |
| Tetrahydrofolate | LP_HC | Positive | 1.60 | 0.03 | 2.59 |
| Glutathione | LP_NEC | Negative | 1.39 | 0.00 | 40.51 |
| Nicotinamide | LP_NEC | Negative | 1.29 | 0.00 | 20.81 |
| Butyric acid | LP_NEC | Negative | 1.14 | 0.01 | 8.60 |
| Isobutyric acid | LP_NEC | Negative | 1.21 | 0.00 | 8.89 |
| Lactic acid | LP_NEC | Negative | 1.32 | 0.00 | 11.63 |
| L-lactic acid | LP_NEC | Negative | 1.30 | 0.00 | 6.88 |
| L-phenyllactic acid | LP_MG | Negative | 2.56 | 0.00 | 1.94 |
|  | LP_NEC | Negative | 1.34 | 0.00 | 10.56 |
| 3-indole-lactic acid | LP_NEC | Negative | 1.03 | 0.01 | 1.25 |

Supplementary Explanation:

The preparation method of the fermentation supernatant of *Lactiplantibacillus plantarum* ZFM518 described in Example 5 is obtained by following the procedure in Example 3, specifically as follows: *Lactiplantibacillus plantarum* ZFM518 stored in a freezer at −80° C. was taken out, streaked on MRS solid medium, and anaerobically cultured at 37° C. for 48 hrs. Then, the single colony was picked into 10 mL of MRS liquid medium, and anaerobically cultured at 37° C. for 12 hrs, to obtain a first-generation bacterial culture. 2% of the first-generation bacterial culture was inoculated into 10 mL of MRS liquid medium, anaerobically cultured at 37° C. for 24 hrs, and centrifuged at 4500×g and 4° C. for 10 min. The bacterial precipitation was discarded to finally obtain a fermentation supernatant of ZFM518.

The inventor also conducted the following comparative experiments during the invention process:

Comparative Example 1: The step "anaerobically cultured at 37° C. for 12 hrs, to obtain a first-generation bacterial culture" was modified to "anaerobically cultured at 37° C. for 24 hrs, to obtain a first-generation bacterial culture" while the rest follows the same preparation method as the fermentation supernatant of ZFM518 mentioned above. The resulting product is named fermentation supernatant A of ZFM518.

Comparative Example 2: The step "anaerobically cultured at 37° C. for 24 hrs, and centrifuged at 4500×g and 4° C. for 10 min. The bacterial precipitation was discarded to finally obtain a fermentation supernatant of ZFM518" was modified to "anaerobically cultured at 37° C. for 12 hrs, and centrifuged at 4500×g and 4° C. for 10 min. The bacterial precipitation was discarded to finally obtain a fermentation supernatant of ZFM518" while the rest follows the same preparation method as the fermentation supernatant of ZFM518 mentioned above. The resulting product is named fermentation supernatant B of ZFM518.

Comparative Example 3: Both instances of "anaerobically cultured at 37° C." were modified to "anaerobically cultured at 28° C." while the rest follows the same preparation method as the fermentation supernatant of ZFM518 mentioned above. The resulting product is named fermentation supernatant C of ZFM518.

Comparative Example 4: Both instances of "anaerobically cultured at 37° C." were modified to "anaerobically cultured at 30° C." while the rest follows the same preparation method as the fermentation supernatant of ZFM518 mentioned above. The resulting product is named fermentation supernatant D of ZFM518.

Comparative Example 5: Both instances of "anaerobically cultured at 37° C." were modified to "anaerobically cultured at 40° C." while the rest follows the same preparation method as the fermentation supernatant of ZFM518 mentioned above. The resulting product is named fermentation supernatant E of ZFM518.

Comparative Example 6: The step "2% of the first-generation bacterial culture was inoculated" was modified to "1% of the first-generation bacterial culture was inoculated" while the rest follows the same preparation method as the fermentation supernatant of ZFM518 mentioned above. The resulting product is named fermentation supernatant F of ZFM518.

The fermentation supernatants A through E were subjected to "Inhibition of Lactiplantibacillus plantarum ZFM518 on Klebsiella pneumoniae ZFM4" test according to the method described in Example 5. The pH of the above fermentation supernatants was measured using a pH meter, and the comparative results of the effects are as follows:

TABLE 3

Comparative experimental results

| Experimental subject | Diameter of antibacterial zone (mm) | pH |
|---|---|---|
| Fermentation supernatant (Example 5) | 20.76 ± 1.09 | 3.76 |
| Fermentation supernatant A (Comparative Example 1) | 16.58 ± 0.66 | 3.77 |
| Fermentation supernatant B (Comparative Example 2) | 15.42 ± 0.73 | 3.89 |
| Fermentation supernatant C (Comparative Example 3) | 13.03 ± 1.02 | 4.03 |
| Fermentation supernatant D (Comparative Example 4) | 14.72 ± 0.69 | 3.95 |
| Fermentation supernatant E (Comparative Example 5) | 17.85 ± 0.84 | 3.81 |
| Fermentation supernatant F (Comparative Example 6) | 16.70 ± 0.84 | 3.88 |

This experiment conducted comparative studies on the preparation method of the fermentation supernatant of Lactiplantibacillus plantarum ZFM518 to evaluate its inhibitory effect on Klebsiella pneumoniae ZFM4 under different cultivation conditions. The study compared variations in culture time, temperature, and inoculation volume, with the inhibition zones and pH values used to assess the outcomes.

The results indicate the following:

The standard method (Example 5) produced the most significant inhibitory effect, with an inhibition zone diameter of 20.76±1.09 mm and a pH of 3.76.

Extending the first-generation bacterial culture time to 24 hrs (Comparative Example 1) and reducing the second-generation bacterial culture time to 12 hrs (Comparative Example 2) both resulted in a decreased inhibitory effect, suggesting that an optimal culture time is crucial for maintaining antimicrobial activity.

Lowering the culture temperature to 28° C. or 30° C. (Comparative Examples 3 and 4) further weakened the inhibitory effect, especially at 28° C., where the inhibition zone diameter dropped to 13.03±1.02 mm. This indicates that temperature plays a significant role in the metabolic activity of the strain and the production of inhibitory substances.

Raising the temperature to 40° C. (Comparative Example 5) resulted in a slightly stronger inhibitory effect compared to other comparative experiments but was still lower than the standard method, indicating that excessively high temperatures negatively impact the antimicrobial activity.

Reducing the inoculation volume to 1% (Comparative Example 6) also led to a diminished inhibitory effect, demonstrating that a sufficient initial bacterial population is essential for the effective production of inhibitory substances.

In summary, the standard cultivation method exhibited the optimal inhibitory effect. Deviations from these conditions significantly impacted the antimicrobial activity of the Lactiplantibacillus plantarum ZFM518 fermentation supernatant against Klebsiella pneumoniae ZFM4. This highlights that culture time, temperature, and inoculation volume are all critical factors influencing antimicrobial activity during the fermentation process.

Finally, it is to be noted that only several specific embodiments of the present application are described above. Apparently, the present application is not limited to the above embodiments, and many variations can be made. All variations that can be directly deduced by or occur to those skilled in the art based on the disclosure of the present application are considered to be contemplated in the protection scope of the present application.

What is claimed is:

1. A method of treating a subject infected by Klebsiella pneumoniae strain ZFM4 deposited under CCTCC NO: M 20221900, the method comprising a step of exposing an infected area of the subject to a composition comprising a therapeutically effective amount of a fermentation supernatant of a Lactiplantibacillus plantarum strain ZFM518 deposited under CCTCC NO: M 2022442.

2. The method of claim 1, wherein the fermentation supernatant is obtained according to the following steps:
    (a) inoculating a single colony of the Lactiplantibacillus plantarum strain ZFM518 into MRS liquid medium and anaerobically culturing at 37° C. for 12 hours to obtain a first-generation bacterial culture;
    (b) inoculating 2% of the first-generation bacterial culture into MRS liquid medium and anaerobically culturing at 37° C. for 24 hours;
    (c) centrifuging the cultured medium at 4500×g and 4° C. for 10 minutes to obtain a bacterial precipitate; and
    (d) discarding the bacterial precipitate to obtain the fermentation supernatant of ZFM518.

3. The method of claim 2, further comprising the step of filtering the fermentation supernatant to remove any residual cells or debris.

* * * * *